United States Patent [19]

McGrath et al.

[11] 4,216,462
[45] Aug. 5, 1980

[54] PATIENT MONITORING AND DATA PROCESSING SYSTEM

[75] Inventors: William J. McGrath, Delafield; Regis P. DiGiacomo, Wauwatosa, both of, WI

[73] Assignee: General Electric Company, Milwaukee, Wis.

[21] Appl. No.: 883,730

[22] Filed: Mar. 6, 1978

[51] Int. Cl.² .................. H04Q 9/00; H04J 3/00; G06F 3/05
[52] U.S. Cl. .................. 340/150; 128/710; 364/415; 128/904
[58] Field of Search .................. 340/151, 150, 182, 163, 340/189, 147, 146.1 AB; 364/900, 415; 346/33 ME; 128/2.1 A; 178/68, 2 C

[56] References Cited
U.S. PATENT DOCUMENTS

| | | | |
|---|---|---|---|
| 3,812,337 | 5/1974 | Crosley et al. | 340/146.1 AB |
| 3,898,373 | 8/1975 | Walsh | 178/2 C |
| 3,908,641 | 9/1975 | Judson et al. | 346/33 ME |
| 3,910,257 | 10/1975 | Fletcher et al. | 128/2.1 A |
| 3,925,762 | 12/1975 | Heitlinger et al. | 340/150 |
| 3,961,139 | 6/1976 | Bowman et al. | 179/15 AL |
| 4,019,172 | 4/1977 | Srodes | 340/163 |
| 4,033,336 | 7/1977 | Murawski et al. | 346/33 ME |
| 4,047,159 | 9/1977 | Boudry | 340/150 |
| 4,051,522 | 9/1977 | Healy et al. | 128/2.1 A |

*Primary Examiner*—Donald J. Yusko
*Attorney, Agent, or Firm*—Dana F. Bigelow

[57] ABSTRACT

The system is composed of a plurality of bedside stations, each in the vicinity of a hospitalized patient, and each interconnected to a central station for monitoring and controlling the bedside stations. The bedside stations contain a plurality of physiological sensing and data sending modules. Each bedside unit contains a central processor for controlling the flow and format of data from the module and to the central station. The central station includes peripheral display units for selectively displaying data from each of the bedside stations. A central processor controls the flow of data from each bedside station to the peripheral displays and for communicating with each bedside processor. Data links are provided for the analog data from the central stations and data links for serial asynchronous data transmission from the bedside station to the central station and for commands from the central station to the bedside station. The waveforms from the bedside stations are frequency modulated through optical couplers to isolate the electric currents between each bedside station while delivering a distortion-free signal. The physiological sensing and data sending modules each include addressable memory which identifies the module to the bedside processor and the central processor. The system includes instructions which automatically perform diagnostic analysis of the circuitry of the system and at regular intervals. The system can be serviced by inserting a diagnostic memory board which displays questions that require responses by an operator which sequentially checks out all circuitry and peripherals of the system.

6 Claims, 8 Drawing Figures

PATIENT MONITORING AND DATA PROCESSING SYSTEM

BACKGROUND OF THE INVENTION

This invention relates to a system for acquiring, processing, storing, transmitting and displaying data relative to the physiological condition of a critically ill patient in a hospital.

The first generation prior art of patient monitoring apparatus comprised sensors attached to the patient to provide analog signals such as the electrocardiogram (ECG), blood pressure, temperature and others. Detected analog signals were amplified and processed, and displayed essentially as analog signals on devices such as oscilloscopes, calibrated meters and strip chart recorders. Initially, these apparatus were located at the bedside of the patient. In more advanced installations a number of bedside units were connected to a central station which had analog display devices. This permitted medical personnel at the central station to monitor the dynamic wave forms of several patients simultaneously. Whenever a certain monitored parameter from a certain patient exceeded a preset limit, and audio alarm notified medical personnel of the problem. Thus, the first generation of patient monitoring apparatus was primarily a collection of analog units, each performing a single function.

The first generation patient monitoring systems had several disadvantages. Amont them is that data could not be stored in the best form. Only dynamic wave forms could be stored and reviewed later when some alarm condition occurred. Data transmission was limited, and a separate analog line was required for each wave form and each derived parameter which was to be transmitted from any bedside to a central station. Any communication from the central station to the bedside station required separate analog lines from those used to transmit physiological data from the bedside to the central station. Further disadvantages were that the amount of display hardware needed to monitor the patient became excessive, distracting and was more difficult for medical personnel to monitor.

A second generation of patient monitoring apparatus was designed to overcome some of the disadvantages in data processing, storage and displaying inherent in the first generation of patient monitoring systems. The second generation system added a central computer to the previously existing bedside and central station units. The system was thus endowed with the capability for deriving more complex, physiological parameters by way of computer programs, storing derived parameters for later review by medical personnel, and generating graphs and/or hard copy of stored data.

Among the disadvantages of the second generation systems were that they had the same limitations on data transmission between the bedside and central station units as did the initial systems. An additional set of analog lines were required to transmit each distinct wave form and each distinct derived parameter to the central processor. A separate set of digital lines were required from the central processor to the digital display. The second generation systems also lacked a capability for convenient expansion. Additional amplifiers, processors, display devices and/or modifications of existing display devices were required to expand the system.

A significant improvement in patient monitoring systems, was described in U.S. Pat. No. 3,925,762 to Heitlinger, et al and assigned to the same assignee as the present invention. This prior art system utilized a central processor in the central station and could accomodate up to four bedside stations. A distinctive feature of the above system was the use of a set of digital data busses and digital interfaces for two-way transmission of all data between all units in the system. The system was inherently computer compatible because all of the data was communicated in digital format. All data sources converted information into digital words before transmission and all receivers read digital words. The data sources or senders throughout the system had binary counters which began counting simultaneously upon occurrence of a synchronizing pulse which was applied to all of them at the same time so that they all counted in synchronism. Generated data words each had a time slot which was identified by a count number with respect to a count initiating sync pulse. The words were gated into the data busses synchronously and repetitively. The receivers had counters which were all synchronized by the same sync pulse as were the senders so that they counted correspondingly. Any receiver which was designated to receive a particular word counted the same number as did the sender when the data was gated onto the bus and the receiver was controlled by a logic system, as was the sender, to open its gates simultaneously to enter and store the data during its short appearance on the bus.

The above system provided some distinct features and advanced the patient monitoring art. However, the system was limited to four bedside stations for each central station, and the system was extremely complex and expensive.

SUMMARY OF THE INVENTION

Accordingly, one general object of the present invention is to provide a system for accurately and efficiently acquiring, deriving, storing, communicating and displaying patient data.

Another object is to provide a patient data system capable of monitoring many bedside stations at a central station.

Another object is to provide physiological data sensing and transmitting modules which can be interchangeable to expand or modernize the bedside station and remain compatible with the central station.

Another object is to transfer data using multiple microprocessors and asynchronous techniques which avoid the expensive timing and synchronizing circuitry.

Another object is to provide a system which completely isolates the electrical currents between each bedside station and the central station.

Another object is to provide a system where the data from the bedside station is free of distortion after transmission to the central station.

Still a further object is to provide a system which is automatically self-diagnosing for malfunction within the system.

These and other objects are accomplished by the invention in which a patient monitoring system employs a multiple microprocessor network and asynchronous data transmission.

The system is comprised of a plurality of bedside stations, each in the vicinity of a hospitalized patient, and each interconnected to a central station for monitoring and controlling the bedside stations. The bedside stations contain a plurality of physiological sensing and data sending modules. Each bedside unit contains a central processor for controlling the flow and format of data from the module and to the central station. The central station includes peripheral display units for selectively displaying data from each of the bedside stations. A central processor controls the flow of data from each bedside station to the peripheral displays and for communicating with each bedside processor. Data links are provided for the analog data from the central stations and data links for serial asynchronous data transmission from the bedside station to the central station and for commands from the central station to the bedside station. The waveforms from the bedside stations are frequency modulated through optical couplers to isolate the electric currents between each bedside station while delivering a distortionfree signal. The physiological sensing and data sending modules each include addressable memory which identifies the module to the bedside processor and the central processor. The system includes instructions which automatically perform diagnostic analysis of the circuitry of the system and at regular intervals. The system can be serviced by inserting a diagnostic memory board which displays questions that require responses by an operator which sequentially checks out all circuitry and peripherals of the system.

BRIEF DESCRIPTION OF THE DRAWINGS

While the novel features of the invention are set forth with particularity in the appended claims, the invention will be better understood along with other objects and features thereof, from the following detailed description taking in conjunction with the drawings in which:

DESCRIPTION OF A PREFERRED EMBODIMENT

Figure 1:
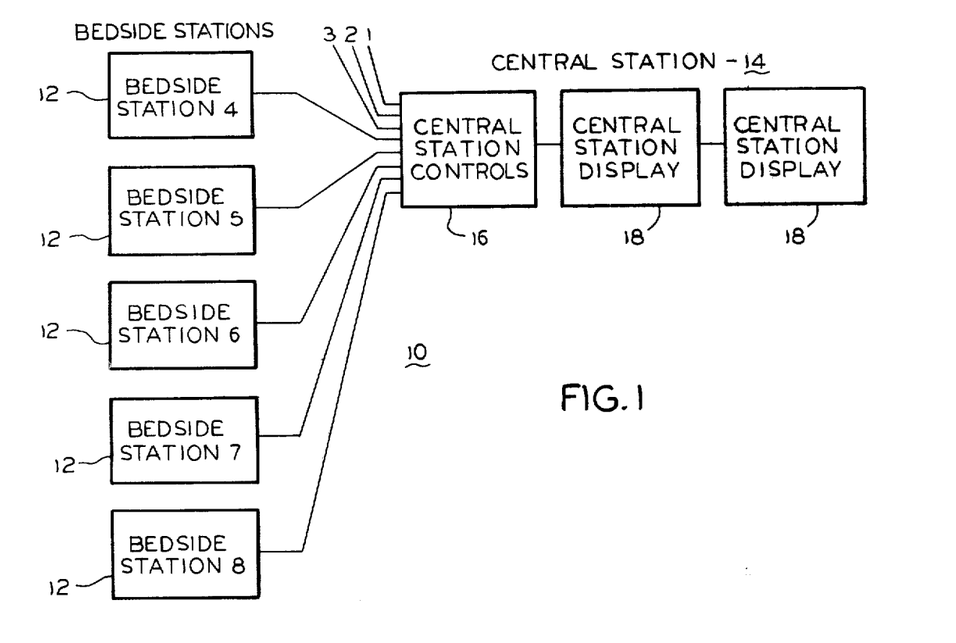
FIG. 1 is a block diagram of the arrangement of the bedside stations interconnected to a central station of the patient monitoring and data processing system.
Figure 2:
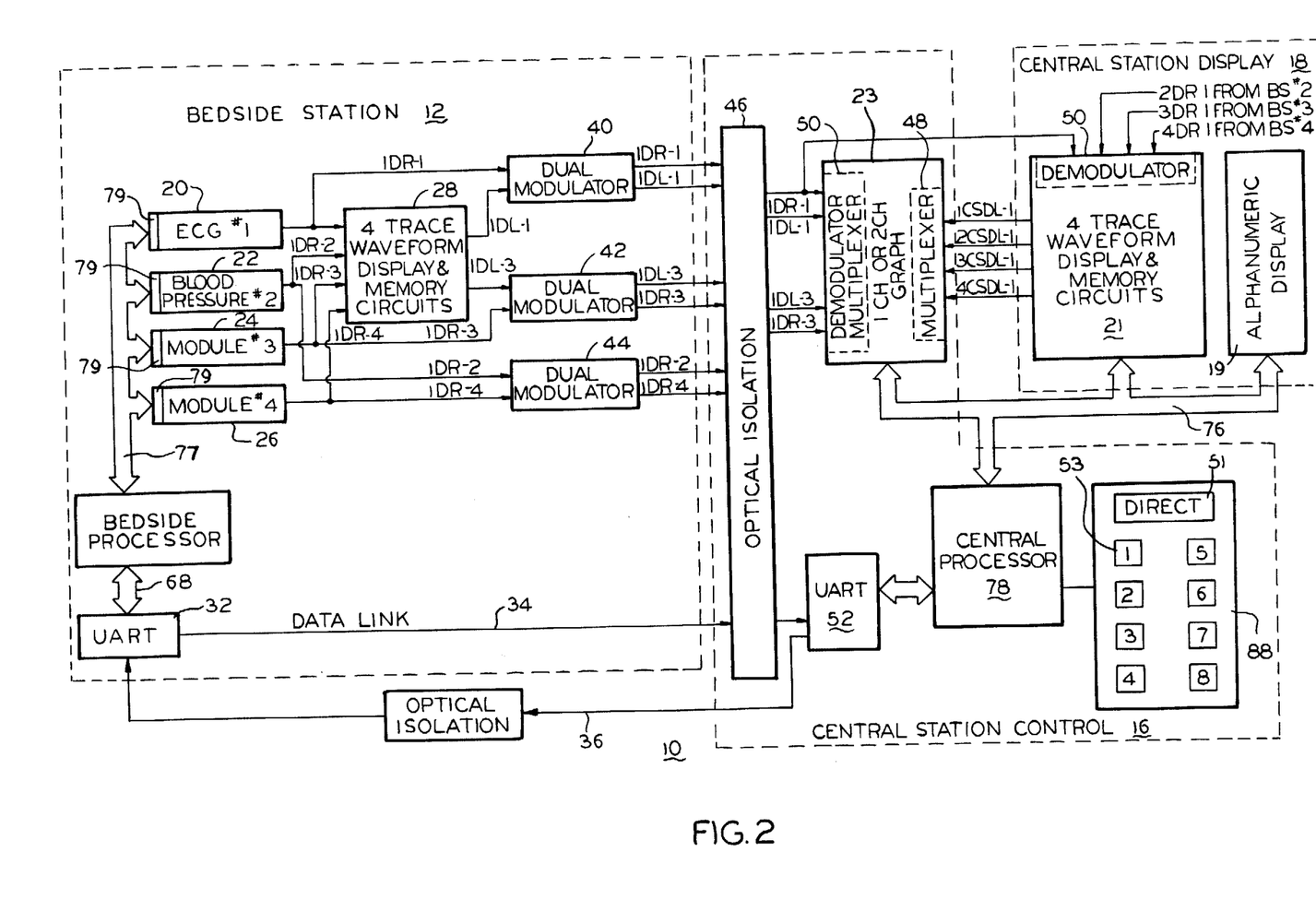
FIG. 2 is a block diagram of the elements of a typical bedside station and the central station of the system.

Referring first to FIGS. 1 and 2, there are shown the general arrangement of the patient monitoring and data handling system 10. The system comprises up to eight bedside stations generally defined by a solid or dashed lined block marked 12, and the central station 14 including a central station control 16 and central station displays 18, generally defined by solid or dashed lined blocks. The bedside stations 12 may be separated from the central station 14 by a considerable distance in a hospital. The multiple bedside stations 12 are located in proximity with each patient who requires the close medical surveillance which the system is intended to provide. Each bedside station 12 has the capability for deriving physiological information about a patient, displaying the information and transmitting and receiving information to and from the central station 14. Some examples of the physiological data derived by the bedside stations 12 include electrocardiograph (ECG), blood pressure, heart rate, temperature and the like. Each bedside station can house a four trace, nonfade display and house up to four physiological sensor modules. Each bedside station 14 interfaces with central station control 16, which is essentially an eight patient automatic graph. Two central station displays 18 are located at central station 14 along with the central station control 16. Each central station display 18 contains an alphanumeric display 19 and a four trace, nonfade display 21. Parameter data originating from up to four bedside stations is presented on each alphanumeric display 19 in addition to visual system and physiological alarm indicators. Each four trace display 21 presents a primary waveform originating from up to four bedside stations, and the two central station displays 18 allow display capability for up to eight bedside stations.

The system provides for the physiological sensing units to be of the plug-in/pull-out modularity configuration for ease of system expansion and ease of reconfiguration. For instance, physiological modules, such as ECG, module 20 and blood pressure, module 22, can be easily plugged into or pulled out of the bedside station 12. Since the degree and type of monitoring that is performed at any bedside varies, plug-in/pull-out modularity allows quick configuration that is compatible with the monitoring needs of the patient. In addition, system down time due to servicing can be minimized by quickly exchanging a defective module for a good one while the defective module is being serviced.

The system provides the bedside station 12 and central station 14 with waveforms (ECG and blood pressure), digital data, physiological alarms and system alarms. LED readouts, alphanumeric messages and audible tones alert the operator when a physiological or system alarm occurs. Central station graph 23 provides 2 strip chart recorders for permanently recording the waveform data. Alphanumeric labeling is printed along the margin of the strip chart, depicting whether the graph is operating in a direct or delayed waveform mode; also, bed number, time, date, and module parameter name and value are printed in the margin of the strip chart.

Figure 5:
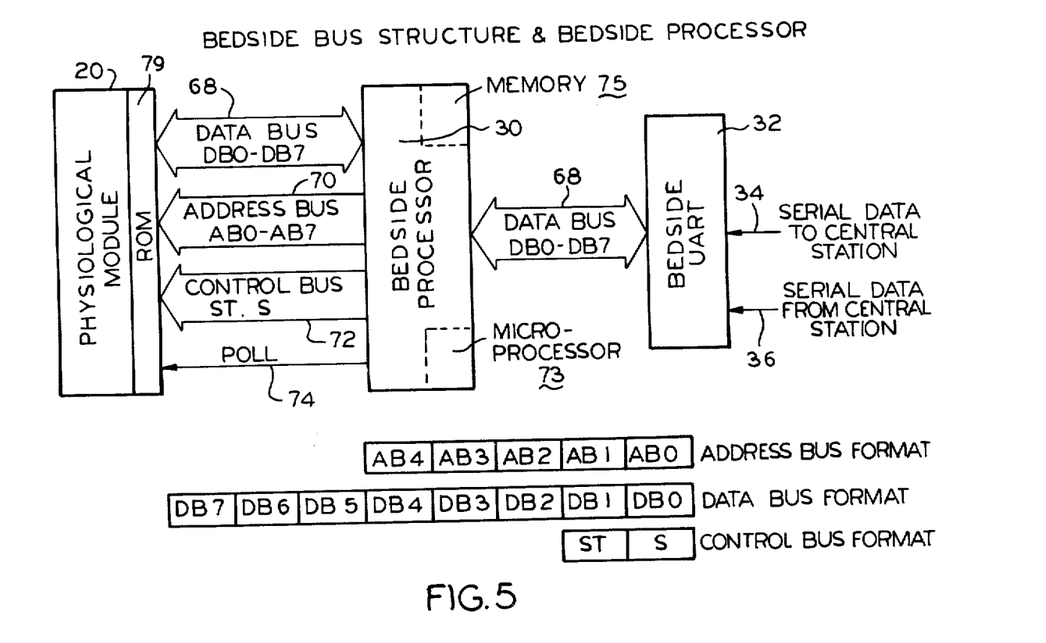
FIG. 5 is a block diagram of the communication structure and format of a bedside station.

Referring particularly to FIGS. 2 and 5, there is shown the basic configuration for a typical bedside station 12. Bedside station 12 is capable of accepting four plugin/pull-out physiological modules identified as block 20, 22, 24 and 26, and contains a four trace display 28. Each bedside station 12 also contains a bedside processor 30 and a universal asynchronous receiver/transmitter (UART) 32. Each bedside station 12 has an interface which allows communication cable connection between the bedside station and central station 14. This communication cable provides the digital data link 34 from the central station 14 to the bedside station 12, and digital data link 36 from the bedside station to the central station.

There are six waveform channels between each bedside station 12 and the central station 14. Four direct waveform channels designated DR1, DR2, DR3, and DR4 and two delayed waveform channels designated DL1 and DL2, which transmit the waveform data to central station 14 for subsequent processing and presentation on the central station graph 23 and the central station four traced display 21. The waveform travels from right to left on the display. A direct waveform is the real time output of a physiological module, such as ECG or blood pressure. A bedside delayed waveform is a bedside waveform output that has been delayed by memory circuits in the bedside four trace display 28. The waveform is delayed for six seconds before being transmitted to the central station 14. A delayed waveform appears as the waveform information that exits the far left trace of the display 21. The signal appearing at the right edge of the display 21 represents real time and the signal disappearing at the left edge of the display represents what happened six seconds prior. All waveform outputs from modules 20, 22, 24 and 26 are frequency modulated (FM) prior to reaching central station 14. Three dual modulator circuits represented by blocks 40, 42, and 44, located in each bedside station, FM modulates the physiological waveform of each of the six channels. Suitable modulators are available as model XR-2207 "voltage-controlled oscillator" from R-OHM Corporation, Irvine, California. When the FM waveforms reach central station, they are optically coupled to the central station circuitry and designated by optical isolation block 46, located within the central station control 16. The FM modulation effectively negates the inherent non-linear characteristics of commercially available optical isolators. A waveform signal varying in amplitude and coupled through an optical isolator would undergo severe amplitude distortion unless costly and complex circuitry is employed to compensate for the distortion. No signal distortion occurs to the frequency components. The FM modulated waveform thereby avoids signal distortion.

Figure 3:
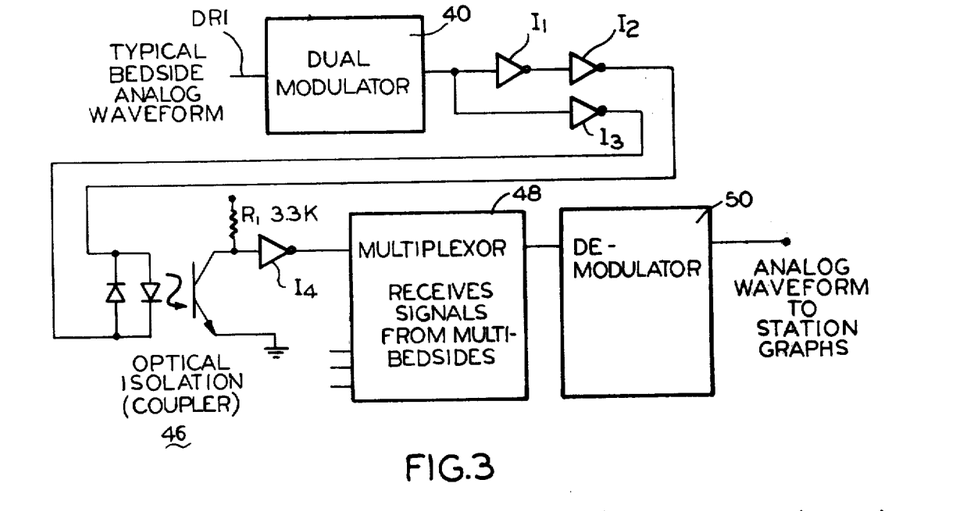
FIG. 3 is a logic diagram showing the optical coupling between each of the bedside stations and the central station of the system.

Referring particularly to FIG. 3, there is shown the logic diagram of a waveform from a bedside station going through optical isolation 46 to central station 14. Dual modular 40 receives the analog waveform and modulates a square wave having a center frequency of 1,650 Hertz. The modulated signal is taken differentially through an inverting buffer I1, and through inverters I2 and I3. Each FM waveform is input to optical isolation 46 (optical coupler) which consists of a light emitting diode (LED) which light couples signal information to a phototransistor which drives the central station processing circuitry. The LED emits infrared light in proportion to the signal current (FM Signal) through it. Light of varying intensity drives the base of the photo transistor which provides a varying signal to the rest of the system. Optical coupling is used to minimize leakage current that may result due to the difference in potential between the bedside and central ground systems. A suitable optical isolation system is available from Monsanto Corporation as "dual photoransistor opto-isolator," model MCT-6. After the FM waveforms are optically coupled to central station 14, a multiplexer 48 multiplexes and a demodulator 50 demodulates the waveform. A suitable multiplexer is available as model DG501 from Siliconix Corporation. The analog waveform can now be printed out on the central station graph 23.

Referring again to FIG. 2, there is shown an additional class of delayed waveform which can be printed out on the central station graph in addition to the bedside direct and bedside delayed waveforms. The third class of waveforms are the primary (those from the uppermost module of each bedside station) direct waveforms designated 1DR1, 2DR1, 3DR1, etc., and which are FM demodulated by demodulator 50, and delayed by the memory circuits of the four trace display 21 at central station control 16. The direct primary waveform from the bedside stations which have been demodulated and delayed by the central station four trace display 21 are designated as 1CSDL-1, 2CSDL-1, 3CSDL-1, etc.

The following example may illustrate the use of the direct and delayed waveforms. If a nurse wants a hard copy printout of an ECG waveform depicting how a patient is doing now, she depresses a button labled DIRECT 51 and a respective patient select button 53 on the front of the central station control 16. The graph prints out the exact ECG waveform as the electrical activity in the patient's heart generates it at this exact moment in time. Now on the other hand, is a physiological alarm suddenly occurs at bedside, the central station graph is automatically initiated. The nurse or doctor wants to know the patient's heart activity prior to the alarm condition. The six second delay provided by the memory circuits in the bedside display allows the strip chart to show what was going on six seconds prior to the alarm.

Figure 4:
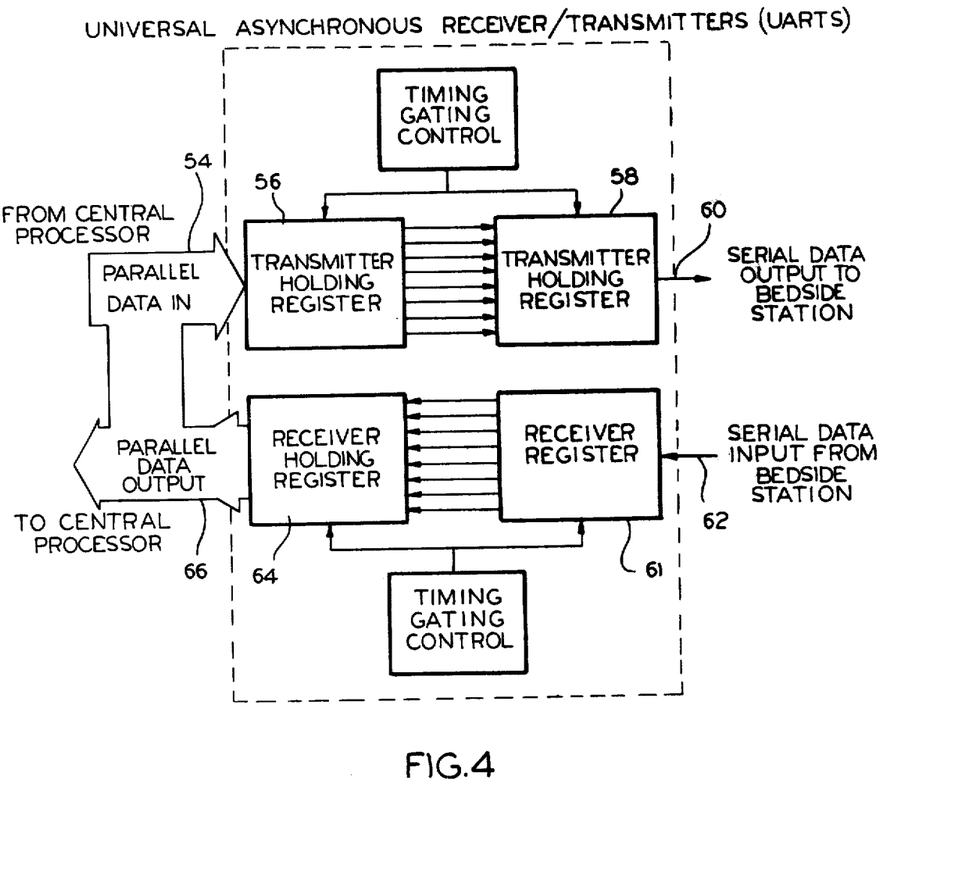
FIG. 4 is a block diagram of a universal asynchronous receiver/transmitter.

Referring to FIGS. 2, 4 and 5, there are shown the data transmission paths of the system. Digital data communication between bedside station 12 and central station 14 is accomplished by a bidirectional, asynchronous hard-wired connection. Serial digital data is transmitted from bedside to central station on data link 34 which consists of a single twisted pair of wires, and from central station to bedside station on data link 36 which consists of another twisted pair of wires. The information transmitted over data link 34 is the sensor module parameter digital data and system control commands. The data links operate at a data transmission rate of 30 characters per second. The encoding of data, commands, etc., uses the well known standard seven bit ASCII code. Each command is defined uniquely by a printable ASCII character. The digital information is bit serial, word serial, and asynchronous. The word length is 10 bits composed of one start bit, seven character bits (ASCII code), one parity bit and one stop bit. Odd parity is used for error detection.

The universal asynchronous receiver transmitter (UART) device is provided and shown as bedside UART 32 and a central station UART 52 to convert parallel data on the data busses to serial data for transmission over the data links. As shown in FIG. 4, parallel data 54 enters the transmission holding 56 and upon command (enable signals) loads the parallel data into the transmission register 58 where it is shifted out as serial data 60. A receiving register 61 receives serial input data 62 and upon command loads a receiving holding register 64 which outputs parallel data 66. A typical UART suitable to perform the data handling is available as model TR 1402 from Western Digital Corporation, Newport Beach, California.

To further understand the data transmission, refer particularly to FIG. 5 which shows diagrammatically the bedside bus structure and bedside processor. A bedside data bus 68 consists of eight lines for bidirectional data transfer between the bedside processor 30 and one of the physiological modules, such as 20. DB0-DB7 are the mneumonics that depict each of the eight data bus wires. Eight unidirectional wires makeup the bedside address bus 70, designated AB0-AB7. Data is selected by the bedside processor 30 by using five of the address line inputs to a read only memory (ROM) 79 located in each of the physiological modules. A control bus 72 is comprised of two wires which are called the state (S) and strobe (ST) lines, respectively. The state line indicates whether the bedside processor is writing data to a physiological module or is receiving data from the module. The strobe line allows transmission of data between the module 20 and the bedside processor 30. A pole line 74 exists between each bedside station module location and the bedside processor. This separate line allows the bedside processor 30 to select the module with which it communicates.

Figure 6:
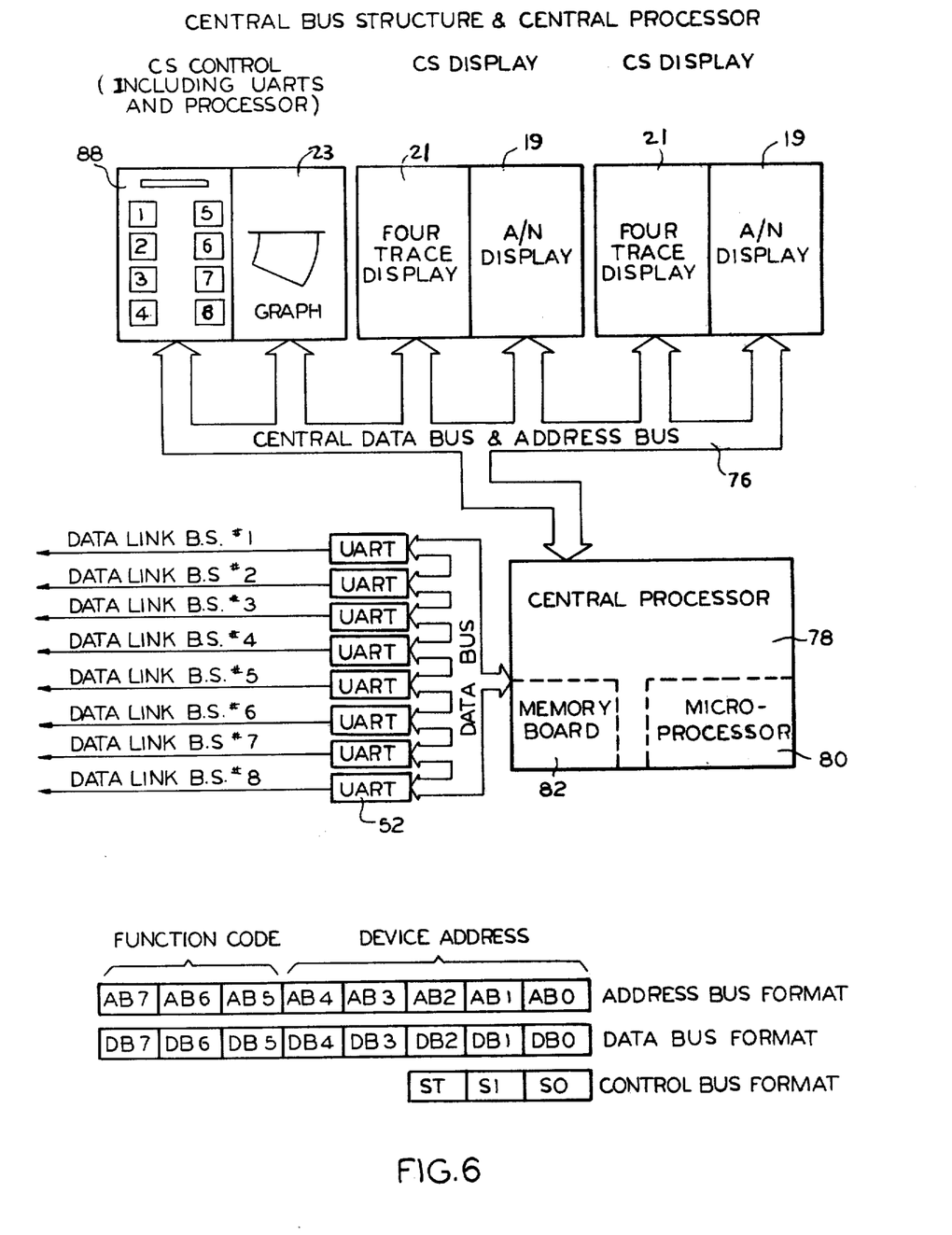
FIG. 6 is a block diagram of the communication structure and format of the central station.

To complete the data transmission communication, refer to FIG. 6, which diagrammatically shows the central bus structure 76 and a central processor 78, which consists of a central microprocessor 80 and a memory board 82. The central processor 78 can handle a maximum of two four trace displays 21, two alphanumeric displays 19, two eight patient shared graphs 23 and eight UARTS 52. As previously discussed the eight UARTS convert parallel data from the central processor to serial data for transmission to each bedside station. Conversely, serial data from each of the eight bedside stations is converted to parallel form by each respective UART for manipulation by the central processor. The central data bus 76 is nineteen wires in width and is divided into three sections, namely the data bus, the control bus and the address bus. The data bus designated DB0-DB7 is comprised of eight wires for bidirectional communication between the central processor 78 and the central station peripherals, such as the four trace display 21 and the alphnumeric display 19. Eight wires also makeup the address bus designated AB0-AB7 which is bidirectional for bits AB0, AB1, AB2, and AB4, and is unidirectional for bits AB3, AB5, AB6, and AB7. The reason for the bidirectional bits is that interrupts are transmitted to the central processor 78 from the central station peripherals over these lines. The unidirectional mode of address lines is used for addressing peripherals in the opposite direction where the same lines are used to transmit interrupts. A device address is established by bits AB0 through AB4. Each peripheral at the central station has a device address code. Address bits AB5 to AB7 are used by the central processor 78 to generate a function code. The function code instructs a specific device to perform certain operations. A control bus allows the central processor 78 to exercise control over the bus through two bus state wires (S0, S1). The control bus line designated ST is used to transmit a strobe pulse. Data transfer between the central processor 78 and the central station peripherals (19, 21, 23 or 88) can only occur when the strobe pulse is LOW.

Having previously established the data communication links and referring particularly to FIGS. 2, 5, the bedside processor 30 can be functionally described. As previously discussed, the purpose of the bedside processor 30 is to interface the physiological modules 20, 22, 24 and 26 to the data links 34 and 36 in order to convey the derived digital parameter information, command and control information, system status indications and patient sensor alarms to a central monitoring location. The beside processor 30 is a complete functional processor on a single printed circuit board. It provides the arithmetic and logic control for the bedside functions and the communications to the central station. The basic elements of the processor include a microprocessor designated by block 73, a memory section designated by block 75 containing read only memory and random access memory, and bedside bus interface designated by 77 which includes 68, 70, 72 and 74 of FIG. 5).

A commonly used microprocessor which is suitable for use in the bedside processor 30 is the Intel 8080. The Intel 8080 microprocessor is a complete eight bit parallel central microprocessing unit for use in general purpose digital computing systems. The Intel 8080 microprocess is fabricated on a single large scale integration chip and can accommodate up to 65K bit of memory. Machine control logic provides a master clock to the bedside microprocessor 73. Control over the bedside system functions is exercised by the microprocessor 73 through control logic. Machine "states" derived by the microprocessor 73 from the master clock are decoded and sent to those parts of the system requiring processing by the machine control logic. The random access memory (RAM) is used for temporary storage of data values computed in response to data link traffic and bedside module requirements. The read only memory (ROM) stores the instructions that guide the processor through operations and decision making. Both the RAM's and the ROM's comprise the memory section 75 of the processor 30, where the microprocessor 73 is the control unit which retrieves instructions from memory and executes them. The bedside bus interface 77 provides the necessary logic for the processor 30 to communicate with the physiological modules 20, 22, 24 and 22 and to the central station 14.

There is a polling line 74 from the bedside processor 30 to each module location. The polling line 74 is a specific addressing scheme that activates the module's bus interface. Only one module can be activated at any one time and only for as long as the data transfer (approximately 2 microseconds). Each physiological module is particular to the parameter it is to monitor. Therefore, the means of identifying its function to the rest of the system is provided within the module and addressable by the bedside processor 30. Since several modules may be installed in the bedside station 12 and there is only one transmission link to the central station 14, the bedside processor must recognize the module. Each module contains the small read only memory 79 and which contains ASCII characters for identification. For example, heart rate contains the characters HR while temperature would contain TEMP. Other specific characters are so contained that identify such occurences as physiological alarm and sensor input failure.

Figure 7:
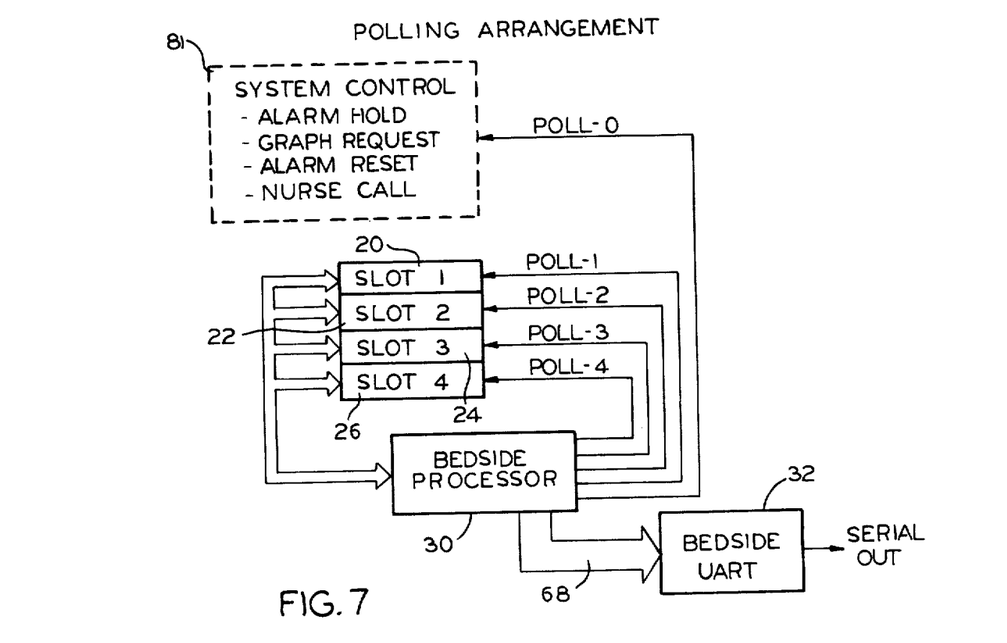
FIG. 7 is a diagram of the scanning of the physiological sensing modules of the bedside station by the bedside processor.

As previously mentioned, the polling line 74 exists between each bedside assembly module location and the bedside processor 30. This polling line is used by the processor 30 to perform data manipulation and data collection. As shown (FIG. 7), the processor 30 polls each module 20, 22, 24 and 26 and the "system controls" 81 (alarm hold, graphy request, alarm reset and nurse call) in the sequence: poll 0-1-2-3-4-0-1-etc. The systems controls 81 are located in each bedside station and addressable to provide operator input to the system. A physiological module is polled when the processor places a LOW on the poll line 74. When this happens, the physiological module places an eight bit status word on the data bus. However, before this can happen, the state line must be in the correct state so that the processor can read the status word. The status words consist of five flag-bits (module off, processing required, data ready, alarm and sensor fail) and three index bits (C0, C1 and C2) used by the bedside processor 30 to compute address locations. The processor 30 reads the status words. The "module off" flag is set LOW when the physiological module is placed in the bedside assembly slot and turned on. When the physiological module is turned off, this bit is set HIGH. When the bedside processor 30 reads this HIGH, it sends a command to central processor 78 to remove the module data from the alphanumeric display 19. When the physiological module is ready to transmit parameter data to central station 14, the "data flag" flag is set LOW. When the data transfer to central station 14 is completed, the bedside processor 30 resets the "data ready" flag to a HIGH. Next the "processor request" flag is tested by the bedside processor after the "data ready" flag is ready. When this flag is set to LOW, the bedside processor 30 will execute a subroutine located in the ROM 79, contained within the physiological module. After the subroutine is executed, the module has full control of the bedside processor. When a physiological alarm occuurs, DB4 of the status word is set to a LOW. The bedside processor 30 reads this flag bit and allows the transmission of alarm data to central processor 78. Resetting of DB4 is accomplished by the circuitry in the physiological module when the physiological violation is corrected. If the sensor is defective, the "sensor fail" flag of the status word is set to a LOW. When the bedside processor 30 reads the LOW DB3, it allows transmission of the sensor alarm information for processing at the central processor 78. The bedside processor 30 reads the status word that is placed on the data bus by each physiological module. The information content of the status word allows the processor 30 to determine the course of action needed for correcting and processing the data.

Referring to FIG. 6, the central processor 78 is described in terms of function of the central station 14. The central processor 78 is similar to the bedside processor 30 in that the four basic elements are the same, namely: the microprocessor 80, read only memory and random access memory (82), and control bus interface 76. Like the bedside station processor, a suitable controller for the central processor 78 is an Intel 8080 microprocessor. Control logic allows the processor 78 to exercise control over central operations. The central processor 78 is capable of handling up to eight bedside stations 12. Therefore, the system instructions are designated so that the eight bedside stations timeshare the microprocessor 80. Instruction storage resides on the memory board 82 located in the central station control. Both read only memory devices (ROM) and random access memory devices (RAMS) are on the memory board 82. The specialized instruction that allows timesharing of the microprocessor 80 by each bedside station is stored in ROM memory. Temporary storage of data information is achieved by RAM memory. This temporarily stored data is manipulated by the microprocessor 80 as defined by the instructions retrieved from memory 82. One of the major differences between the bedside and central processors is that the central processor 78 operates on an interrupt basis. If a central station peripheral (graph, display, etc.) needs to be serviced by the central processor 78, the peripheral sends out an interrupt which is latched in to the central microprocessor 80. This interrupt forces the microprocessor 80 to stop what it is doing at the time to start a service routine. For instance, an interrupt is transmitted to the the processor 78 when any one of the patient select graph switches 88 on the central station control front panel is depressed. Once the service routine is completed, the central processor 78 returns to the operation from which it was interrupted. When a peripheral device sends out an interrupt, an active LOW signal appears on the appropriate address bus line. Next, the latched-in interrupt is serviced by the interrupt priority and acknowledged circuits. The order of priority of interrupt devices are "clock set" (time/date), "alarm reset," "graph switches," "relative time clock," and "power-up restart."

Figure 8:
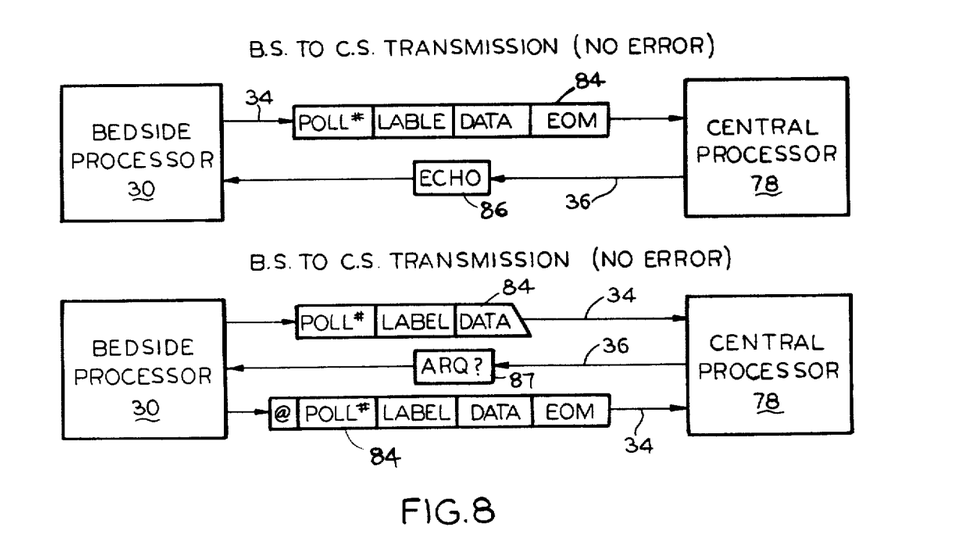
FIG. 8 is a diagram of the serial data format for intercommunication between the bedside processor and the central processor.

Refering now to FIGS. 2 and 8, there is shown the overall scheme of how the central processor 78 communicates with or receives information from the bedside processor 30 using serial asynchronous data transmission 34. Assume that a bedside physiological module 22, 24, 26 or 28 is ready to transmit data. The bedside processor 30 will first transmit the poll number. When the central processor 78 receives the poll number, it will dedicate one of the segments of the alphanumeric display 19 for presenting parameter data for that particular bedside station. Next, after the poll number, the bedside processor 30 sends the parameter label (SYST for systolic blood pressure), followed by the data values, followed by the end of message code. The central processor 78 echoes on line 36 each character back to the bedside processor 30 unless a transmission error is detected. FIG. 8 also shows the transmission scheme having a transmission error detected by the central processor. The central processor 78 detects parity error, framing error and overrun errors. The ten bit serial word uses odd parity as one type of error detection. Framing error applies to the situation where a valid stop bit was not transmitted with the ten bit serial word. If the central processor detects an error, it sends the character "?" back to the bedside processor. This character "?" stands for automatic request for repeat (ARQ) 87. When the bedside processor 30 receives the ARQ message 87, it then sends a message interrupt character to the central processor 78 to acknowledge the request for repeat and cancel the erring message. Then the bedside processor 30 restates the transmission starting with the poll number, etc.

A particularly useful instruction provides self diagnosis of the system by the processors. The self diagnosing instruction is done automatically and is designated to detect the subtle faults that would normally escape routine functional testing. The central station processor 78 executes the diagnostic instruction each time the power is turned on and again at eight o'clock a.m. every day from then on. The bedside processor 30 also executes a self diagnosing instruction when power is turned on and every 24 hours thereafter. This self diagnostic test is performed without any interruption to the normal monitoring functions. The test time requires approximately 100 milliseconds and concentrates on the processor circuitry and the data bus that interconnects the bedside station modules 20, 22, 24 and 26 to the central station 14. The testing instructions are designed to test the processor device, the temporary storage memory and the istruction storage memory. Implicit in the operation of the above tests is a check of the data bus, since data must flow to and from each section over the data bus connections. The processor executes a specific sequence of instructions that are designated to detect certain types of device function faults. These type of faults can occur internal to the devices temporary data registers and its ability to properly sequence through the instructions. The second section of the test exercises the temporary storage (RAM) memory devices. Patterns are written into this memory and read back for comparison. Each memory cell is tested three times under different logical conditions before it is considered operative. The third test is a check on the contents of the instruction storage devices. The system instructions are stored in read only memory (ROM) so that no loss of instructions will occur when power is turned off. An operation called "check summing" is performed on these memory devices to insure that no instructions have changed since the ROM's were initially programmed at the factory. If an error is found in any part of the testing, the central station processor 78 will display, on the alphanumeric module display 19, a system malfunction message followed by an error code number. This number indicates to the service engineer the particular circuit where the fault was discovered. The bedside processor 30 communicates its errors to the central station 14 so that the central station process will display a flashing warning message. Both messages will also print out on the graph end printer 23 whenever the graph is in operation.

The system also utilizes an insertable instruction called the DIAGNOSTIC MEMORY BOARD (DMB). This is a service tool that is, basically, a printed circuit board with memory devices that contain a system level diagnostic program. The board is designed to replace the standard computer instructions in the central station processor 78 in order to test the functions of the central stations in bedside digital systems. In effect, the processor 78 is reprogrammed by insertion of the DMB to exercise all of these functions in conjunction with an operator. The tests were ordered in the following sequence: (a) test graph switch control panel, (b) test alphanumeric display, (c) test freeze/unfreeze/cascade operation of the wave form display, (d) test audio alarm tone/alarm reset function, (e) test graph operation/status/edge printer function, (f) test bedside communication/microcomputer. The DMB begins the tests automatically and lights the first graphs switch and expects the operator to press the switch. This procedure verifies that the switch pressed agrees with the switch lamp the microprocessor lighted. The processor extinguishes the lamp if there are no errors. The alphanumeric display 19 is the second device tested. Each character location is exercised as well as the full character set generator in the display. After the key board switches and the alphnumeric displays have been verified, they may be used as input and output devices for the remaining tests. Instructions for the following tests are given to the operation by the microprocessor by way of the alphnumeric display 19. The responses required from the operator are entered using the graph control keyboard, thus no special test instruments are required to operate the DMB.

The processor 78 is required to unfreeze the waveform display 21 under certain conditions during normal operation. This permits the graph to record from memory. In order for the processor to determine which waveform trace must be unfrozen it must also read the status of the cascade switches. Thus, the waveform display test exercises this function by requesting that the operator freeze the traces. The processor will then proceed to unfreeze each trace individually and display the status of the cascade switches for operation verification. Following this test, the processor will turn on the audio alarm tone and instruct the operator to press the alarm reset pushbutton. If this test is successful, the processor will start the graph recorder 23, and print on the edge of the paper three times the full character set. Thus, the graph start/stop and edge printing functions are tested. The processor will also display the graph status so that the operator may verify that the graph controls (e.g. direct, power on, 20/40 second time out) are functioning correctly. The final test requires no operation intervention. The central processor 78 will send a command to each bedside processor 30 to execute its internal mini-diagnostic. Following the mini-diagnostic the bedside processor 30 will send its first message from any input function module (20) to the central station 14. This message is analyzed by the DMB for correct format, transmission errors, and timing. If the message is received satisfactorily the central microcomputer will display "I'm okay—Bedside test completed." Should an error be detected, the appropriate error message is displayed in order to assist the service engineer in locating the source of the fault.

In between each test the operator is given the option, through the graph control keyboard, of repeating the test that was just completed. This permits more detailed analysis should a failure be detected. Thus, the central processor can be used as a digital signal generator. Generally, a system may be functionally verified in just a few minutes.

It will thus be apparent that the present patient monitoring and data processing system provides a system for accurately and efficiently acquiring, displaying and communicat ing data for many bedside stations to a central station. The system utilizes FM modulation of the output waveforms for distortion-free transmission through optical couplers which completely isolate the electrical currents between each bedside station and the central station. The system provides for automatic self-diagnosis for any malfunctions within the system.

While a specific embodiment of the present invention has been illustrated and described herein, it is realized that modifications and changes will occur to those skilled in the art. It is therefore to be understood that the appended claims are intended to cover all such modifications and changes as fall within the true spirit and scope of the invention.

What is claimed is:

1. An improved patient monitoring and data handling system having a plurality of bedside stations, each for location in the vicinity of a hospitalized patient and each interconnected to a central station having at least one peripheral display unit for displaying monitored data from said bedside stations, wherein each said bedside station includes a bedside processor having a central processing unit for controlling the flow and format of data from said bedside station to said central station; and said central station includes a central processor having a central processing unit for controlling the flow of data from said bedside stations to said peripheral display unit and for communicating with said beside processors.

2. A patient monitoring and data handling system having a plurality of bedside stations, each for location in the vicinity of a hospitalized patient and each interconnected to a central station for monitoring and communicating with each said bedside station, with each said bedside station comprising a plurality of opening adapted to receive at least one physiological sensing and data sending module and a bedside processor having a central processing unit for controlling the flow and format of data from said modules to said central station, and with said central station comprising at least one peripheral display unit for selectively displaying data from one of said bedside stations and a central processor having a central processing unit for communication with said bedside processor and with each said module having addressable memory which identifies said module to the respective bedside central processing unit and to the central processor and permits each said module to be interchangeable within any of the openings in any of said bedside stations, and such that the addressable memory of each of said module expands the memory of the respective said bedside processor.

3. The system as recited in claim 2 wherein each said bedside station and said central station include a universal asynchronous receiver-transmitter and data links for serial asynchronous bi-directional intercommunication over the same data links between each said bedside processor and said central processor.

4. The system as recited in claim 2 wherein data signals from said bedside stations are interconnected through optical coupling means to said central station, thereby electrically isolating bedside stations and said central station.

5. The system as recited in claim 2 wherein said central processor and each said bedside station processor includes means for performing diagnostic checks of the circuitry of the system each time the system is turned on and at regular intervals thereafter, including pattern checks of the addressable memory of each said bedside processor and said central processor, check-sum testing of the memory and functional checks of each central processing unit, and means for displaying any system malfunctions.

6. The system as recited in claim 2 which further includes means for servicing the system comprising a diagnostic memory board adapted to be plugged into said central station, said memory board providing a series of displayed requests and questions which reqire responses by an operator which sequencially checks out the circuitry and peripherals of the system, including a test of a graph switch control, a test of an alphanumeric display, a test of an alarm, a test of a waveform graph operation of said peripheral display unit and a test of each said bedside and said central processor units.

* * * * *